(12) United States Patent
Yonezawa et al.

(10) Patent No.: US 10,955,663 B2
(45) Date of Patent: Mar. 23, 2021

(54) LOG INFORMATION COLLECTION METHOD AND INFORMATION PROCESSING APPARATUS

(71) Applicant: FUJITSU LIMITED, Kawasaki (JP)

(72) Inventors: Kazuya Yonezawa, Kawasaki (JP); Ryuta Tanaka, Machida (JP)

(73) Assignee: FUJITSU LIMITED, Kawasaki (JP)

(*) Notice: Subject to any disclaimer, the term of this patent is extended or adjusted under 35 U.S.C. 154(b) by 0 days.

(21) Appl. No.: 16/437,885

(22) Filed: Jun. 11, 2019

(65) Prior Publication Data

US 2020/0012094 A1 Jan. 9, 2020

(30) Foreign Application Priority Data

Jul. 5, 2018 (JP) .............................. JP2018-128550

(51) Int. Cl.
| | |
|---|---|
| *G06F 3/01* | (2006.01) |
| *G02B 27/00* | (2006.01) |
| *A61B 5/024* | (2006.01) |
| *G02B 27/01* | (2006.01) |

(52) U.S. Cl.
CPC .......... *G02B 27/0093* (2013.01); *A61B 5/024* (2013.01); *G02B 27/017* (2013.01); *G06F 3/013* (2013.01); *G02B 2027/014* (2013.01); *G02B 2027/0138* (2013.01); *G02B 2027/0187* (2013.01)

(58) Field of Classification Search
None
See application file for complete search history.

(56) References Cited

U.S. PATENT DOCUMENTS

| | | | |
|---|---|---|---|
| 10,237,304 B1* | 3/2019 | Sokolov | G06F 3/011 |
| 2004/0171460 A1* | 9/2004 | Park | A63B 24/0087 482/8 |
| 2006/0022833 A1* | 2/2006 | Ferguson | A63B 24/0003 340/573.1 |
| 2008/0208016 A1* | 8/2008 | Hughes | A61B 5/0533 600/301 |
| 2010/0207877 A1* | 8/2010 | Woodard | G09G 5/00 345/156 |
| 2013/0103624 A1* | 4/2013 | Thieberger | G06N 5/046 706/12 |
| 2014/0184550 A1* | 7/2014 | Hennessey | G06F 3/013 345/173 |
| 2015/0220814 A1* | 8/2015 | Verkasalo | G06Q 20/3255 382/103 |
| 2015/0317801 A1* | 11/2015 | Bentley | G08B 21/043 382/107 |
| 2017/0076486 A1* | 3/2017 | Aizawa | G06F 1/163 |

FOREIGN PATENT DOCUMENTS

JP  2017-68851  4/2017

* cited by examiner

*Primary Examiner* — Parul H Gupta
(74) *Attorney, Agent, or Firm* — Staas & Halsey LLP

(57) ABSTRACT

An information processing apparatus includes a processor configured to: determine whether a state of a user that views a virtual space is a predetermined state, based on state information indicating the state of the user and condition information for determining that the user is in the predetermined state; and start collection of log information upon determining that the state of the user is the predetermined state.

12 Claims, 14 Drawing Sheets

| ITEM | CONDITION | |
|---|---|---|
| VIEWPOINT RETENTION TIME | ○ SECONDS OR MORE | 420-1 |
| SOUND VOLUME | × dB OR MORE | 420-2 |
| HEART RATE | ×× TIMES OR MORE | 420-3 |

| OBJECT TYPE | ITEM | CONDITION |
|---|---|---|
| SOUND SOURCE | POSITION | POSITION IS WITHIN PREDETERMINED RANGE FROM SOUND SOURCE AND OTHER CONDITIONS ARE NOT MET |
| BUILDING, SPACE | VIEWPOINT | VIEWPOINT IS DIRECTED FOR CERTAIN PERIOD OF TIME/ POSITION OF VIEWPOINT IS MOVED WITHIN OBJECT |
| | POSITION | POSITION INSIDE OBJECT |
| OBJECT | VIEWPOINT | VIEWPOINT IS DIRECTED FOR CERTAIN PERIOD OF TIME/ POSITION OF VIEWPOINT IS MOVED WITHIN OBJECT |
| | POSITION | POSITION WITHIN PREDETERMINED RANGE FROM OBJECT |
| SOURCE OF SMELL | POSITION | POSITION WITHIN PREDETERMINED RANGE FROM OBJECT |

| OBJECT TYPE | ITEM | SELECTION METHOD |
|---|---|---|
| SOUND SOURCE | POSITION | PREDETERMINED RANGE WITHIN WHICH SOUND MAY BE HEARD |
| BUILDING, SPACE | VIEWPOINT | SAME DIRECTION AS VIEWPOINT |
| | POSITION | PREDETERMINED RANGE |

LOG INFORMATION COLLECTION METHOD AND INFORMATION PROCESSING APPARATUS

CROSS-REFERENCE TO RELATED APPLICATION

This application is based upon and claims the benefit of priority of the prior Japanese Patent Application No. 2018-128550, filed on Jul. 5, 2018, the entire contents of which are incorporated herein by reference.

FIELD

The embodiments discussed herein are related to a log information collection method and an information processing apparatus.

BACKGROUND

For the purpose of improving the quality of virtual reality (VR) content in a virtual space, it has recently been desired to understand the degree of user's attention to an object or area disposed in the virtual space.

As a technology to understand the degree of the user's attention, for example, a technology has been known that acquires the viewpoint or position of the user in the virtual space as log information and displays an image indicating the viewpoint of the user, a heat map indicating a history of movement of the user, or the like by superposition thereof on the VR content for visualization.

Related techniques are disclosed in, for example, Japanese Laid-open Patent Publication No. 2017-68851.

With the conventional technology, the object or area to which the user has turned his/her eyes within the virtual space may be determined from the acquired log information. However, it is difficult to determine whether the user has turned his/her eyes to the object or area in curiosity or for no special reason. With the conventional technology, the position where the user has stayed may be detected from the log information. However, it is difficult to determine whether the user has stayed in the position on purpose or for no special reason.

With the conventional technology, it is difficult to acquire log information when the degree of the user's attention is increased in the virtual space.

SUMMARY

According to an aspect of the embodiments, an information processing apparatus includes a processor configured to: determine whether a state of a user that views a virtual space is a predetermined state, based on state information indicating the state of the user and condition information for determining that the user is in the predetermined state; and start collection of log information upon determining that the state of the user is the predetermined state.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 16A and 16B are diagrams illustrating an example of selection condition information according to a third embodiment.

DESCRIPTION OF EMBODIMENTS

First Embodiment

Figure 1:
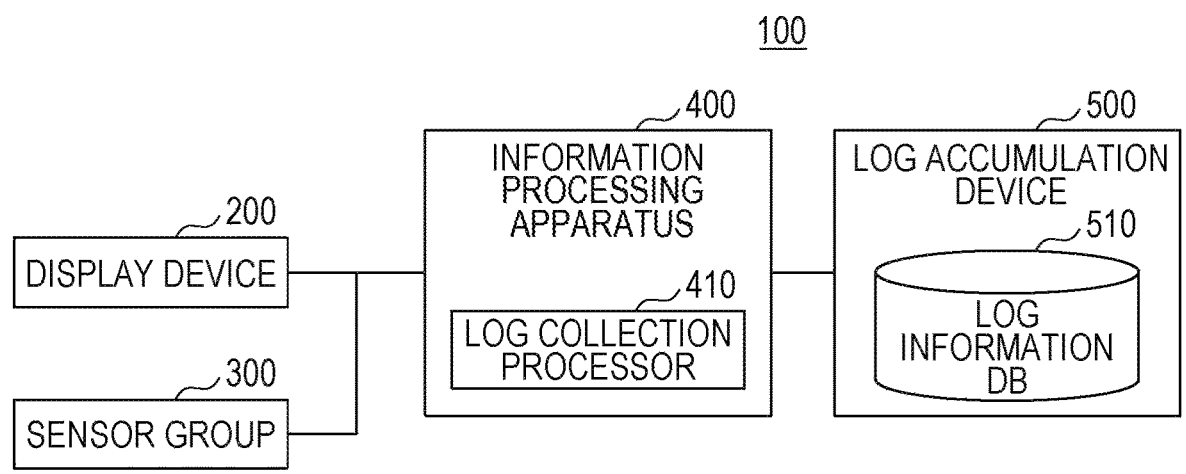
FIG. 1 is a diagram illustrating an example of a virtual space presentation system according to a first embodiment.

Hereinafter, a first embodiment is described with reference to the drawings. FIG. 1 is a diagram illustrating an example of a virtual space presentation system according to the first embodiment.

A virtual space presentation system 100 according to the present embodiment includes a display device 200, a sensor group 300, an information processing apparatus 400, and a log accumulation device 500.

In the virtual space presentation system 100 according to the present embodiment, the display device 200 and the sensor group 300 are coupled by wire or wirelessly to the information processing apparatus 400. In the virtual space presentation system 100, the information processing apparatus 400 is coupled by wire or wirelessly to the log accumulation device 500.

The display device 200 according to the present embodiment is, for example, a head mounted display (HMD) or the like, which is mounted on a user's head to present a virtual space to the user. The display device 200 according to the present embodiment may also include a camera to follow the viewpoint of the user wearing the display device 200, a microphone for detecting the voice uttered by the user, and the like. The display device 200 does not have to be the head mounted display but may be any kind of device that may present a virtual space to the user.

The sensor group 300 according to the present embodiment is attached to the user and includes, for example, an acceleration sensor for detecting the movement or rotation of the user's head, a sensor for detecting a heart rate of the user, and the like. Although the display device 200 and the sensor group 300 are separately provided in the example of FIG. 1, the system configuration is not limited thereto. The sensor group 300 may be a part of the display device 200.

The information processing apparatus 400 according to the present embodiment generates an image of the virtual space viewed from the viewpoint of the user, on the display device 200. The virtual space is, for example, a space where objects such as a person and a physical object are virtually arranged in a three-dimensional coordinate space. The information processing apparatus 400 generates an image of the virtual space, based on information such as shapes and positions of the objects.

The information processing apparatus 400 according to the present embodiment includes a log collection processor 410. The log collection processor 410 monitors information acquired from the display device 200 or the sensor group 300, and determines whether or not the user is in a state that triggers to start acquiring log information. When the user is in that state, the log collection processor 410 collects the monitored information, as log information indicating the behavior and state of the user, to store the log information in the log accumulation device 500.

In other words, the information processing apparatus 400 determines, based on the information acquired from the display device 200 or the sensor group 300, whether or not the user is in a state where he/she has become interested in a certain object within the virtual space. When it is determined that the user is in that state, the information processing apparatus 400 starts collecting the log information.

The log information in the present embodiment is, for example, information indicating the viewpoint of the user in the virtual space, the voice uttered by the user, the position of the user within the virtual space, the movement or rotation of the user's head, the heart rate of the user, and the like.

That is, the information processing apparatus 400 monitors, as information indicating the state of the user, the information indicating the viewpoint of the user in the virtual space, the voice uttered by the user, the position of the user within the virtual space, the movement or rotation of the user's head, the heart rate (biological information) of the user, and the like. In the following description, the information monitored by the information processing apparatus 400 is referred to as the monitoring target information.

The log accumulation device 500 according to the present embodiment includes a log information database (DB) 510. The log accumulation device 500 stores the log information acquired from the information processing apparatus 400 in the log information database 510.

Although the virtual space presentation system 100 includes the log accumulation device 500 in the present embodiment, the embodiments are not limited thereto. The log accumulation device 500 may be provided outside the virtual space presentation system 100. Alternatively, the information processing apparatus 400 may also serve as the log accumulation device 500.

Figure 2:
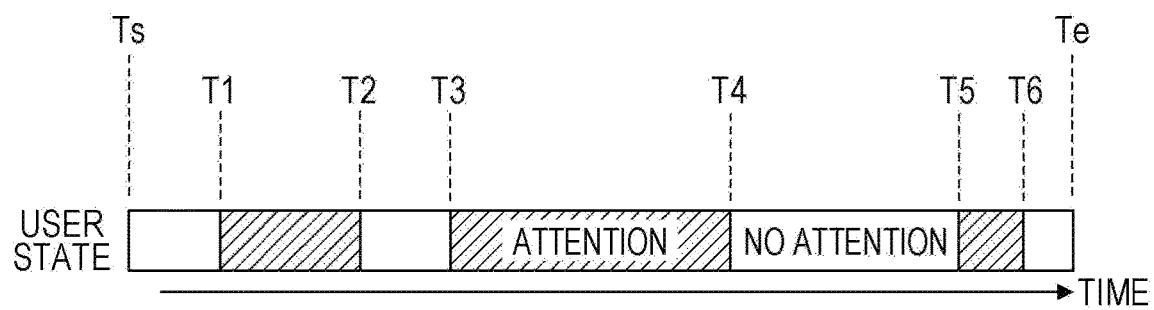
FIG. 2 is a diagram illustrating collection of log information according to a first embodiment.

Hereinafter, with reference to FIG. 2, description is given of collection of log information according to the present embodiment. FIG. 2 is a diagram illustrating collection of log information according to the first embodiment.

FIG. 2 illustrates how the log information is collected when the user enters the virtual space at a time Ts and exits the virtual space at a time Te. In other words, FIG. 2 illustrates how the log information is collected by the information processing apparatus 400 when the presentation of the virtual space to the user wearing the display device 200 is started at the time Ts and the presentation of the virtual space is terminated at the time Te.

Once the presentation of the virtual space is started at the time Ts, the information processing apparatus 400 starts monitoring the monitoring target information acquired from the display device 200 and the sensor group 300.

In FIG. 2, the information processing apparatus 400 determines, based on the monitoring target information, that the state of the user has become a state where the degree of attention to an object or an area within the virtual space is high at a time T1, and starts collecting the log information (monitoring target information). Then, the information processing apparatus 400 determines that the state of the user is no longer the high attention state at a time T2, and terminates the collection of the log information.

In the following description, the state where the degree of user's attention to a certain object or area within the virtual space is increased may be described as the state where the attention to the object or area is high. In the present embodiment, items of information included in the log information do not have to correspond to items of information included in the monitoring target information. The log information may be a part of the monitoring target information, or the monitoring target information may be a part of the log information.

Likewise, between times T3 and T4 and between times T5 and T6, the information processing apparatus 400 determines that the state of the user is the high attention state and thus collects the log information. In the information processing apparatus 400, conditions for determining the high attention state are previously set. These conditions are described in detail later.

As described above, in the present embodiment, whether to collect the log information is determined according to the state of the user during the presentation of the virtual space to the user. For example, in the present embodiment, the collection and accumulation of the log information are performed when it is determined that the state of the user is the high attention state to the object or area within the virtual space during the presentation of the virtual space to the user.

Therefore, according to the present embodiment, log information when the degree of user's attention is increased within the virtual space may be acquired.

Figure 3:
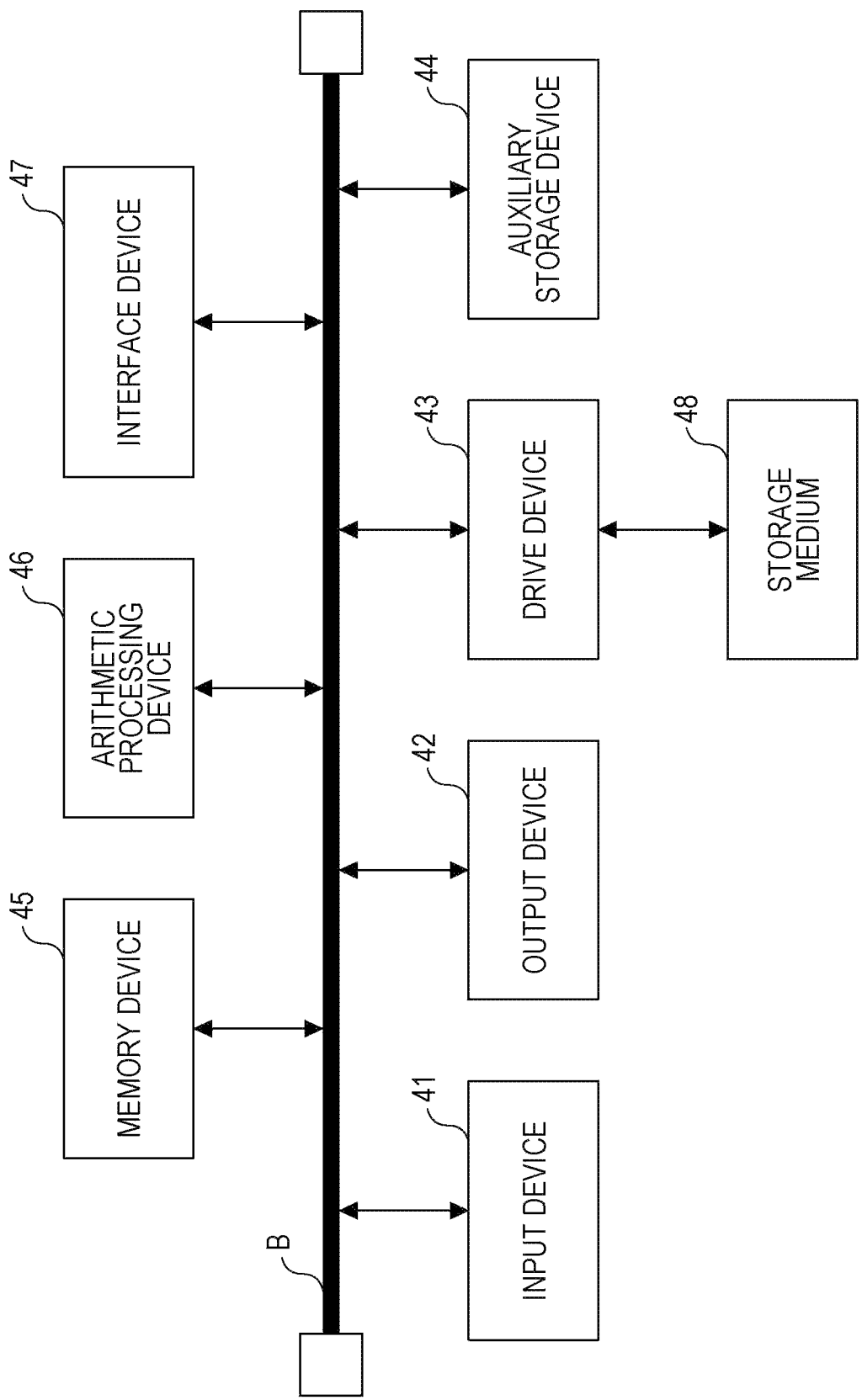
FIG. 3 is a diagram illustrating an example of a hardware configuration of an information processing apparatus according to a first embodiment.

The information processing apparatus 400 according to the present embodiment is described below. FIG. 3 is a diagram illustrating an example of a hardware configuration of the information processing apparatus 400 according to the first embodiment.

The information processing apparatus 400 according to the present embodiment includes an input device 41, an output device 42, a drive device 43, an auxiliary storage device 44, a memory device 45, an arithmetic processing device 46, and an interface device 47. These devices are coupled to each other through bus B.

The input device 41 is a device for inputting various information, which is implemented, for example, by a keyboard, a pointing device, or the like. The output device 42 is for outputting various information, which is implemented, for example, by a display or the like. The interface device 47 includes a local area network (LAN) card or the like and is used for connecting to a network.

An information collection program for implementing the log collection processor 410 is at least a part of various programs for controlling the information processing apparatus 400. The log information collection program is provided, for example, through distribution of a storage medium 48, downloading from the network, or the like. As for the storage medium 48 having the log information collection program recorded thereon, various types of storage media may be used, including a storage medium having information optically, electrically, or magnetically recorded thereon (such as a compact disc read-only memory (CD-ROM), a flexible disk, and a magneto-optical disk), a semiconductor memory having information electrically recorded therein (such as a read-only memory (ROM) and a flash memory), and the like.

As the storage medium 48 having the log information collection program recorded thereon is set in the drive device 43, the log information collection program is installed into the auxiliary storage device 44 through the drive device 43 from the storage medium 48. The log information collection program downloaded from the network is installed into the auxiliary storage device 44 through the interface device 47.

The auxiliary storage device 44 stores the installed log information collection program as well as various desirable files, data, and the like, such as the log information collected by the information processing apparatus 400. The memory device 45 retrieves the log information collection program from the auxiliary storage device 44 at startup of the information processing apparatus 400, and stores the retrieved log information collection program. The arithmetic processing device 46 implements various kinds of processing as described later in accordance with the log information collection program stored in the memory device 45. The arithmetic processing device 46 may be simply referred to as a processor.

Figures 4, 5:
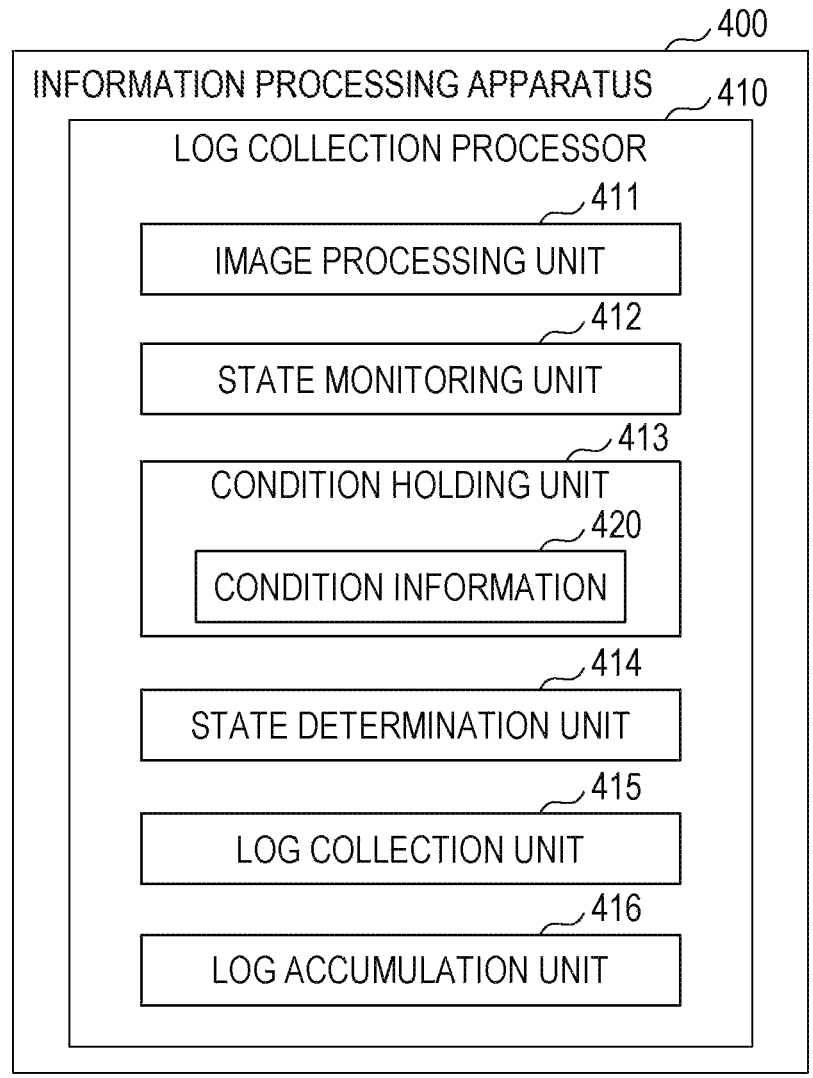
FIG. 4 is a diagram illustrating functions of an information processing apparatus according to a first embodiment.
FIG. 5 is a diagram illustrating an example of condition information according to a first embodiment.

Next, with reference to FIG. 4, description is given of functions of the information processing apparatus 400 according to the present embodiment. FIG. 4 is a diagram illustrating the functions of the information processing apparatus 400 according to the first embodiment.

The information processing apparatus 400 according to the present embodiment includes the log collection processor 410. The log collection processor 410 includes an image processing unit 411, a state monitoring unit 412, a condition holding unit 413, a state determination unit 414, a log collection unit 415, and a log accumulation unit 416.

The image processing unit 411 generates image data indicating an image of a virtual space, based on information such as shapes and positions of objects, and outputs the generated image data to the display device 200. The image processing unit 411 also generates image data indicating the image of the virtual space viewed from the user, in conformity to the movement of the user, and outputs the generated image data to the display device 200.

The state monitoring unit 412 monitors the monitoring target information acquired from the display device 200 and the sensor group 300. The monitoring target information includes, for example, information indicating the viewpoint of the user, information indicating the direction and rotation of the user's head, information indicating the heart rate of the user, information indicating the voice uttered by the user, information indicating the sound volume of the voice, information indicating the position of the user within the virtual space, and the like. The monitoring target information is not limited to the above information. The monitoring target information may be a part of the above information or may include information other than the above information.

The information indicating the viewpoint of the user is information indicating a point on which user's eyes turned to look at an object are focused, and is three-dimensional coordinate information indicating the viewpoint of the user in the virtual space. The coordinate information indicating the viewpoint of the user is obtained, for example, from the virtual space and the viewpoint of the user detected by a viewpoint tracking function or the like included in the display device 200.

The information indicating the position of the user is three-dimensional coordinate information indicating the position of the display device 200 in the virtual space. The information indicating the position of the user may be acquired, for example, when the image processing unit 411 generates the image data indicating the image of the virtual space viewed from the user.

The information indicating the heart rate of the user is, for example, the number of pulses detected by a pulsimeter or the like included in the sensor group 300.

The information indicating the voice uttered by the user and the information indicating the sound volume of the voice are, for example, speech waveforms collected by a microphone or the like included in the display device 200. In the following description, the information indicating the voice uttered by the user and the information indicating the sound volume of the voice may be described as the information indicating the speech waveform.

The condition holding unit 413 sets and holds condition information 420 indicating conditions for determining the state of the user. The condition information 420 is information including conditions indicating that the state of the user is a specific state. The condition information 420 is described in detail later.

The state determination unit 414 determines, based on the condition information 420 and the monitoring target information monitored by the state monitoring unit 412, whether or not the state of the user within the virtual space has become a state where attention to any object or area is high.

The state determination unit 414 also determines, based on the monitoring target information and the condition information 420, whether or not the state of the user is still the high attention state. In other words, the state determination unit 414 determines, based on the information indicating the state of the user acquired from the display device 200 and the sensor group 300, whether or not the state of the user is the specific state.

When it is determined by the state determination unit 414 that the state of the user is the high attention state, the log collection unit 415 starts collecting log information. When it is determined that the state of the user is no longer the high attention state during the collection of the log information, the log collection unit 415 terminates the collection of the log information.

The log information in the present embodiment may at least include the information indicating the position of the user in the virtual space and the information indicating the viewpoint of the user, and does not have to be the same information as the monitoring target information.

The log accumulation unit 416 uploads the log information collected by the log collection unit 415 to the log accumulation device 500 for accumulation.

The log collection unit 415 according to the present embodiment may collect the log information in the form of comma separated value (CSV) files or the like, and the log accumulation unit 416 may upload the CSV files as Hyper Text Markup Language (HTML) format data to the log accumulation device 500.

The data format (CSV format or the like) used to collect the log information and the data format (HTML format or the like) used to upload the log information to the log accumulation device 500 may be previously set in the log collection unit 415 and the log accumulation unit 416.

With reference to FIG. 5, the condition information 420 in the present embodiment is described below. FIG. 5 is a diagram illustrating an example of the condition information according to the first embodiment.

In the condition information 420 according to the present embodiment, items obtained from the monitoring target information are associated with conditions for the items.

In condition information 420-1 illustrated in FIG. 5, the condition "○ seconds or more" is associated with viewpoint retention time. The viewpoint retention time is the time for which the viewpoint is retained at one point or around that point, which is assumed to be the state of the user paying attention to a specific object. For example, a case where the monitoring target information satisfies the condition information 420-1 is considered to be the state of the user paying attention to the specific object.

In condition information 420-2, the condition "× dB or more" is associated with the sound volume. Here, the sound volume is the sound volume of the voice uttered by the user within the virtual space. A case where the sound volume of the user's voice is × dB or more is assumed to be, for example, a state where the user cheers or screams at what he/she sees. For example, a case where the monitoring target information satisfies the condition information 420-2 is considered to be the state of the user having a feeling of wonder, surprise, fear, or the like upon looking at the specific object. In other words, the case where the monitoring target information satisfies the condition information 420-2 may also be said to be a state of the user being distracted by the specific object.

In condition information 420-3, the condition "×× times or more" is associated with the heart rate. A case where the heart rate of the user is ×× times or more is considered to be a state of the user feeling tense or excited. For example, a case where the monitoring target information satisfies the condition information 420-3 may be said to be a state of the user looking at the object while feeling tense or excited.

The condition information 420 illustrated in FIG. 5 is merely an example, and the embodiments are not limited thereto. The condition information 420 may include information indicating association between items and conditions, other than the condition information 420-1 to 420-3 illustrated in FIG. 5.

For example, in the condition information 420, a condition of a predetermined time or more may be associated with the time for which the user utters his/her voices. A state where the user keeps uttering voices is presumably a state of the user giving his/her opinions or views on the object he/she sees.

Figure 6:
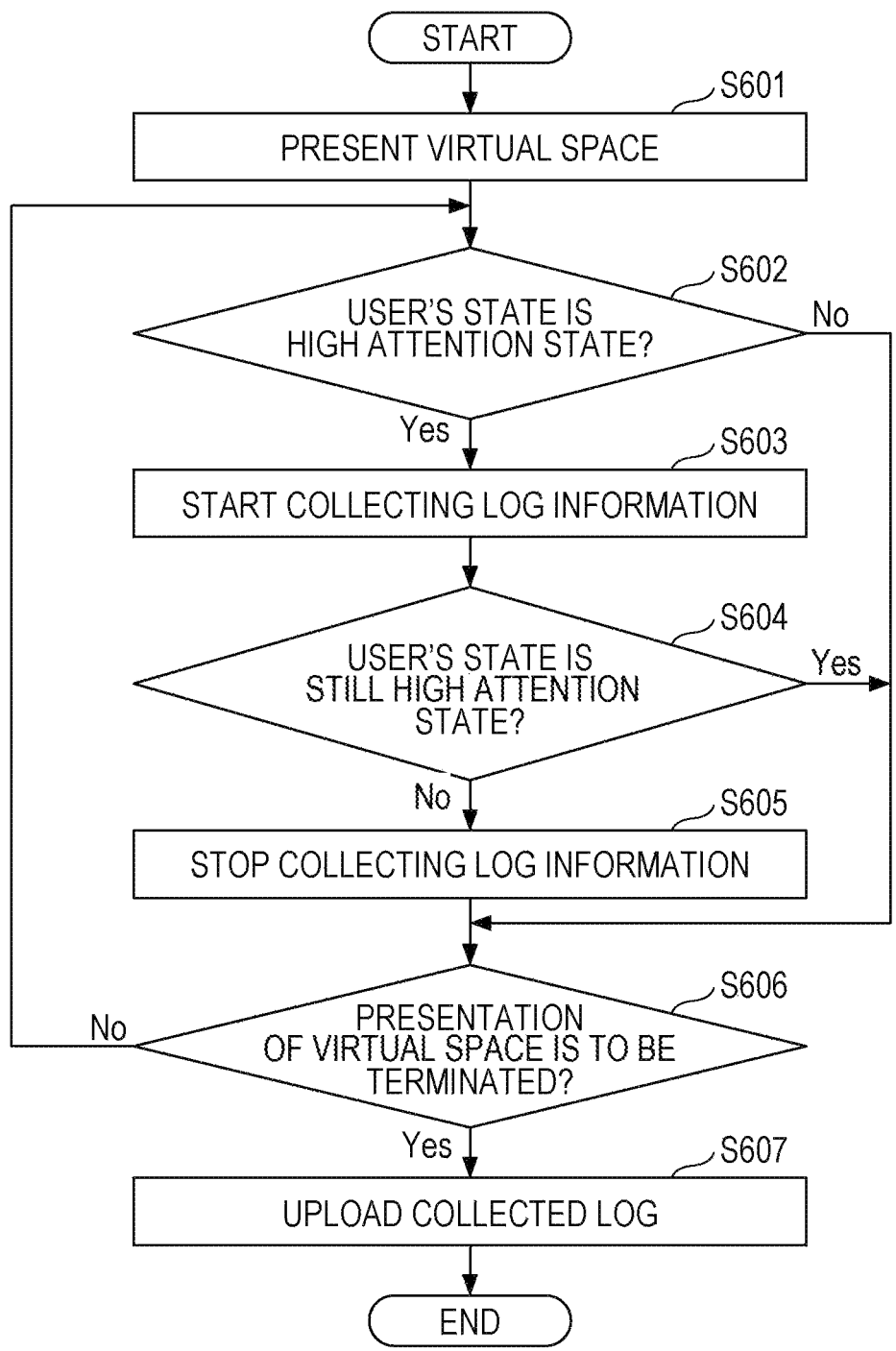
FIG. 6 is a flowchart illustrating operations of an information processing apparatus according to a first embodiment.

Next, with reference to FIG. 6, description is given of operations of the information processing apparatus 400 according to the present embodiment. FIG. 6 is a flowchart illustrating the operations of the information processing apparatus 400 according to the first embodiment.

Upon receipt of an instruction to present a virtual space, the information processing apparatus 400 according to the present embodiment uses the image processing unit 411 to output image data of an image indicating the virtual space to the display device 200, and thus starts presenting the virtual space to the user wearing the display device 200 (Step S601).

The instruction to present the virtual space may be transmitted to the information processing apparatus 400 from the display device 200, for example, as the user puts on the display device 200.

Then, the information processing apparatus 400 uses the state monitoring unit 412 to monitor the monitoring target information outputted from the display device 200 and the sensor group 300, and uses the state determination unit 414 to determine whether or not the monitoring target information satisfies the condition information 420 in the condition holding unit 413 (Step S602). In other words, the state determination unit 414 determines, based on the monitoring target information, whether or not the state of the user is a high attention state.

The determination by the state determination unit 414 in Step S602 is described.

When the monitoring target information satisfies all the conditions indicated by the condition information 420, for example, the state determination unit 414 in the present embodiment may determine that the state of the user is the high attention state.

For example, the state determination unit 414 determines that the state of the user is the high attention state only when the information indicating the viewpoint satisfies the condition information 420-1, the voice uttered by the user and the sound volume of the voice satisfy the condition information 420-2, and the heart rate satisfies the condition information 420-3.

As another implementation, when the monitoring target information satisfies any one of the conditions indicated by the condition information 420, the state determination unit 414 in the present embodiment may determine that the state of the user is the high attention state.

In this case, the state determination unit 414 determines that the state of the user is the high attention state in any of the cases where the information indicating the viewpoint satisfies the condition information 420-1, where the voice uttered by the user and the sound volume of the voice satisfy the condition information 420-2, and where the heart rate satisfies the condition information 420-3, for example.

As still another implementation, when the monitoring target information satisfies more than one of the conditions indicated by the condition information 420, the state determination unit 414 in the present embodiment may determine that the state of the user is the high attention state.

In this case, for example, the state determination unit 414 determines that the state of the user is the high attention state in the case where the information indicating the viewpoint satisfies the condition information 420-1 and the voice uttered by the user and the sound volume of the voice satisfy the condition information 420-2, and in the case where the information indicating the viewpoint satisfies the condition information 420-1 and the heart rate satisfies the condition information 420-3.

In the present embodiment, combinations of the conditions for determining the state of the user to be the high attention state may be previously set in the state determination unit 414.

For example, the state determination unit 414 may be configured to determine the state of the user to be the high attention state only when the monitoring target information satisfies all the conditions indicated by the condition information 420. Alternatively, the state determination unit 414 may be configured to determine the state of the user to be the high attention state when the monitoring target information satisfies a predetermined number of conditions among those indicated by the condition information 420.

When the state of the user is not determined to be the high attention state in Step S602, that is, when it is determined that the state of the user is not the high attention state, the information processing apparatus 400 advances to Step S606 to be described later.

When it is determined in Step S602 that the state of the user is the high attention state, the information processing apparatus 400 uses the log collection unit 415 to start collecting log information (Step S603).

Subsequently, the information processing apparatus 400 uses the state determination unit 414 to determine whether or not the monitoring target information still satisfies the conditions indicated by the condition information 420 (Step S604). In other words, the state determination unit 414 determines whether or not the state of the user is still the high attention state.

The determination by the state determination unit 414 in Step S604 is described.

When the state determination unit 414 in the present embodiment is configured to determine the state of the user to be the high attention state, for example, if a plurality of conditions are satisfied among those indicated by the condition information 420, the state determination unit 414 may determine that the state of the user is no longer the high attention state when any one of the plurality of conditions is no longer satisfied.

For example, when the state determination unit 414 is configured to determine the state of the user to be the high attention state, for example, if the condition information 420-1 and the condition information 420-2 are satisfied, the state determination unit 414 may determine that the state of the user has become a low attention state (state where the attention is not high) once the viewpoint of the user moves to another object and the condition information 420-1 is no longer satisfied.

When it is determined in Step S604 that the attention remains high, that is, when the monitoring target information keeps satisfying the set conditions, the information processing apparatus 400 advances to Step S606 to be described later.

When it is determined in Step S604 that the state of the user is no longer the high attention state, that is, the attention is lowered, the information processing apparatus 400 stops the collection of the log information by the log collection unit 415 (Step S605).

Thereafter, the information processing apparatus 400 determines whether or not to terminate the presentation of the virtual space by the image processing unit 411 (Step S606).

For example, the information processing apparatus 400 may determine to terminate the presentation of the virtual space when the display device 200 is removed from the user's head. Alternatively, the information processing apparatus 400 may determine to terminate the presentation of the virtual space, for example, upon receipt of an instruction to terminate the presentation of the virtual space from outside.

When the presentation of the virtual space is not to be terminated in Step S606, that is, when the presentation of the virtual space is continued, the information processing apparatus 400 returns to Step S602.

When the presentation of the virtual space is to be terminated in Step S606, the information processing apparatus 400 uses the log accumulation unit 416 to upload the collected log information to the log accumulation device 500 to accumulate the log information therein (Step S607), and then terminates the processing.

Figure 7:
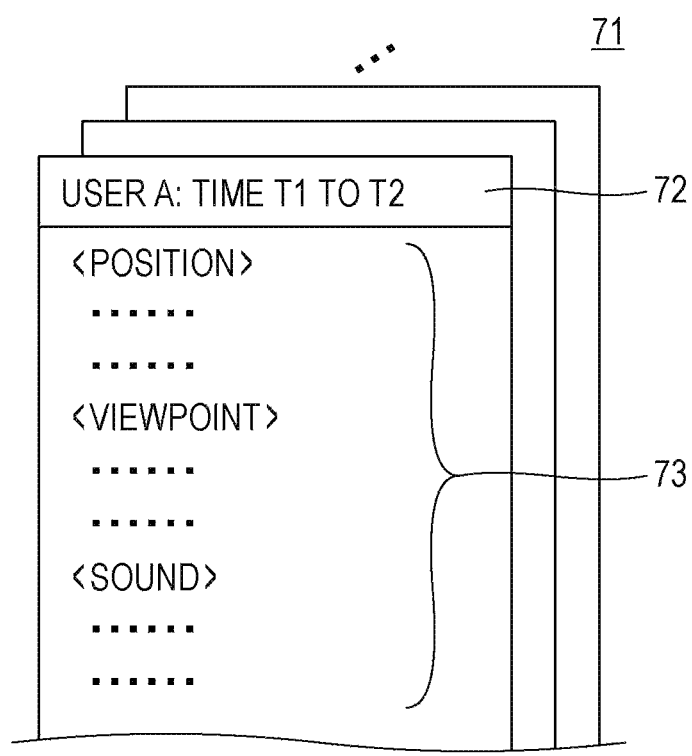
FIG. 7 is a diagram illustrating an example of log information according to a first embodiment.

Hereinafter, with reference to FIG. 7, description is given of the log information collected by the log collection unit 415. FIG. 7 is a diagram illustrating an example of the log information according to the first embodiment.

It is assumed, for example, that log information 71 in the present embodiment is collected for each user. Information for identifying the user may be inputted to and held by the information processing apparatus 400, for example, when the information processing apparatus 400 presents the virtual space to the user through the display device 200.

The log information 71 in the present embodiment includes information 72 and information 73. The information 72 includes user identification information and information indicating a time period during which the log information is collected. The information 73 is information collected by the log collection unit 415.

As may be seen from FIG. 7, the log information 71 includes information indicating the position of a user A within the virtual space, information indicating the viewpoint of the user A, and information indicating the voice of the user A in a time period between times T1 and T2.

As described above, in the present embodiment, it is determined whether or not the user has become a high attention state within the virtual space, based on the information indicating the state of the user acquired from outside the information processing apparatus 400. The information processing apparatus 400 collects log information in a period for which the state of the user is the high attention state.

Therefore, according to the present embodiment, the log information when the degree of user's attention is increased in the virtual space may be acquired.

Second Embodiment

Hereinafter, a second embodiment is described with reference to the drawings. The second embodiment is different from the first embodiment in accumulating log information for each object in association with the object to which a user pays attention, and analyzing the accumulated log information. Therefore, in the following description of the second embodiment, differences from the first embodiment are described, and similar functional configurations to those in the first embodiment are denoted by the same reference numerals used in the description of the first embodiment, and description thereof is omitted.

Figure 8:
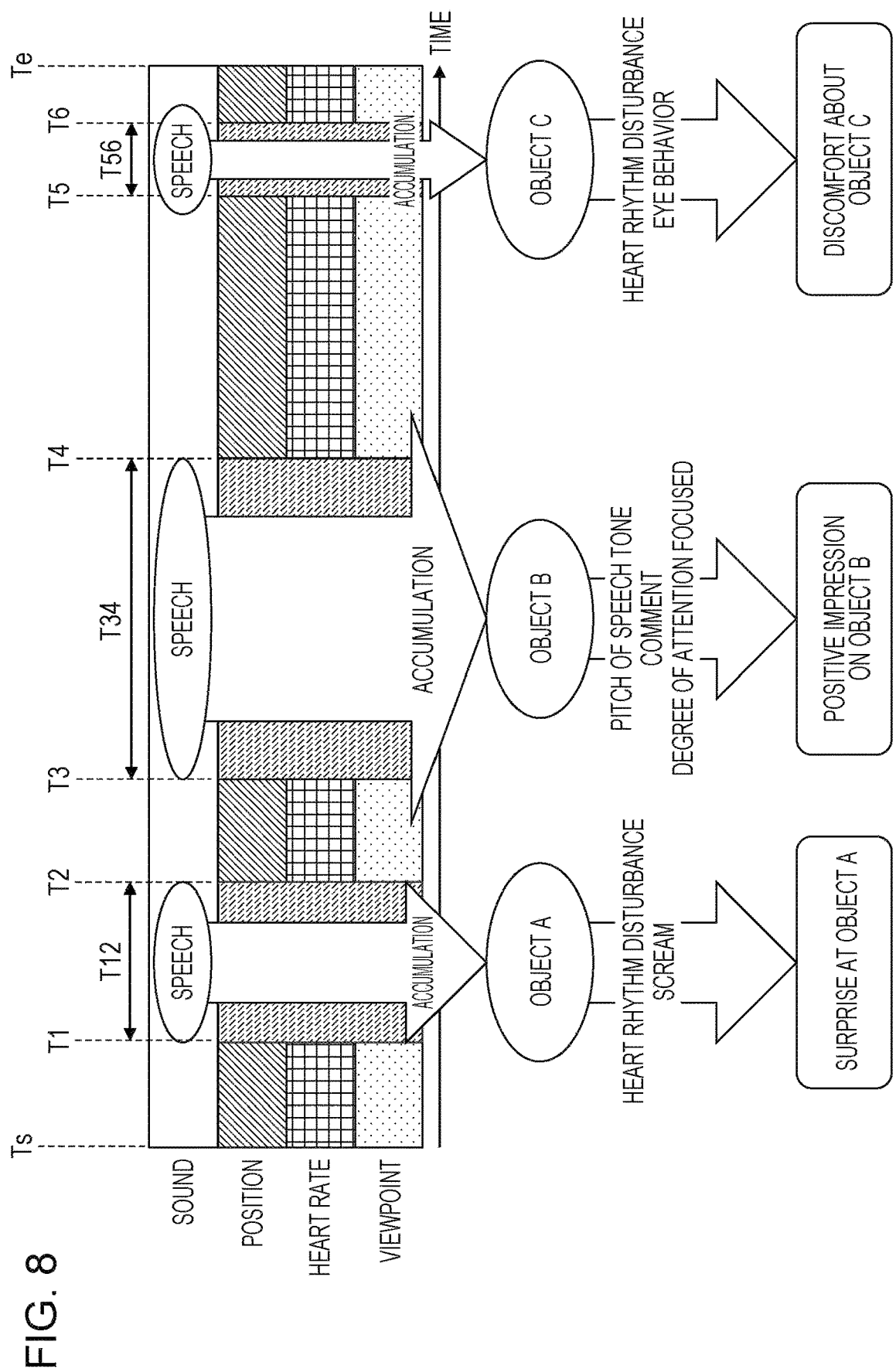
FIG. 8 is a diagram illustrating collection of log information according to a second embodiment.

FIG. 8 is a diagram illustrating collection of log information according to the second embodiment.

FIG. 8 illustrates a case where a virtual space is presented to a user between times Ts and Te, and information indicating a speech waveform, information indicating a position, information indicating a heart rate, and information indicating a viewpoint are collected as log information.

In FIG. 8, the state of the user is determined to be a high attention state in a time period T12 between times T1 and T2, a time period T34 between times T3 and T4, and a time period T56 between times T5 and T6.

In the present embodiment, an object as the target of attention in each time period is selected from among objects in the virtual space, and the log information is accumulated for each selected object. The object as the target of attention may be selected, for example, depending on a positional relationship with the user. The selection of the object is described in detail later.

In the example of FIG. 8, an object A is selected as the target of attention in the time period T12. Therefore, log information collected in the time period T12 is accumulated as user log information for the object A. An object B is selected in the time period T34, and log information collected in the time period T34 is accumulated as log information for the object B. An object C is selected in the time period T56, and log information collected in the time period T56 is accumulated as log information for the object C.

In the present embodiment, the log information accumulated for each object is analyzed for evaluation of the object.

It is assumed, for example, that the log information in the time period T12 indicates that there is disturbance in heart rate of the user, the time for which the voice is uttered is short and the sound volume is large. In this case, it may be seen that the user is surprised at the object A selected in the time period T12. Therefore, an evaluation that the object A may surprise the user is obtained from the log information for the object A.

It is assumed that the log information in the time period T34 indicates that the tone of voice is high, the time for which the voice is uttered is long, and the viewpoint retention time is long. In this case, it may be seen that the user has a good impression on the object B selected in the time period T34. Therefore, an evaluation that the user has a good impression on the object B is obtained from the log information for the object B.

In the present embodiment, for example, text data may be acquired by performing speech recognition on information indicating a speech waveform of the user, and the text data may be acquired as a part of the log information.

It is assumed that the log information in the time period T56 indicates that there is disturbance in heart rate of the user and the viewpoint stays on the object C for a short time more than once. In this case, it may be seen that the user is looking away from or trying not to look for a long time at the object C selected in the time period T56. Therefore, an evaluation that the object C makes the user uncomfortable is obtained from the log information for the object C. In other words, an evaluation is obtained that the user has a bad impression of the object C.

Figure 9:
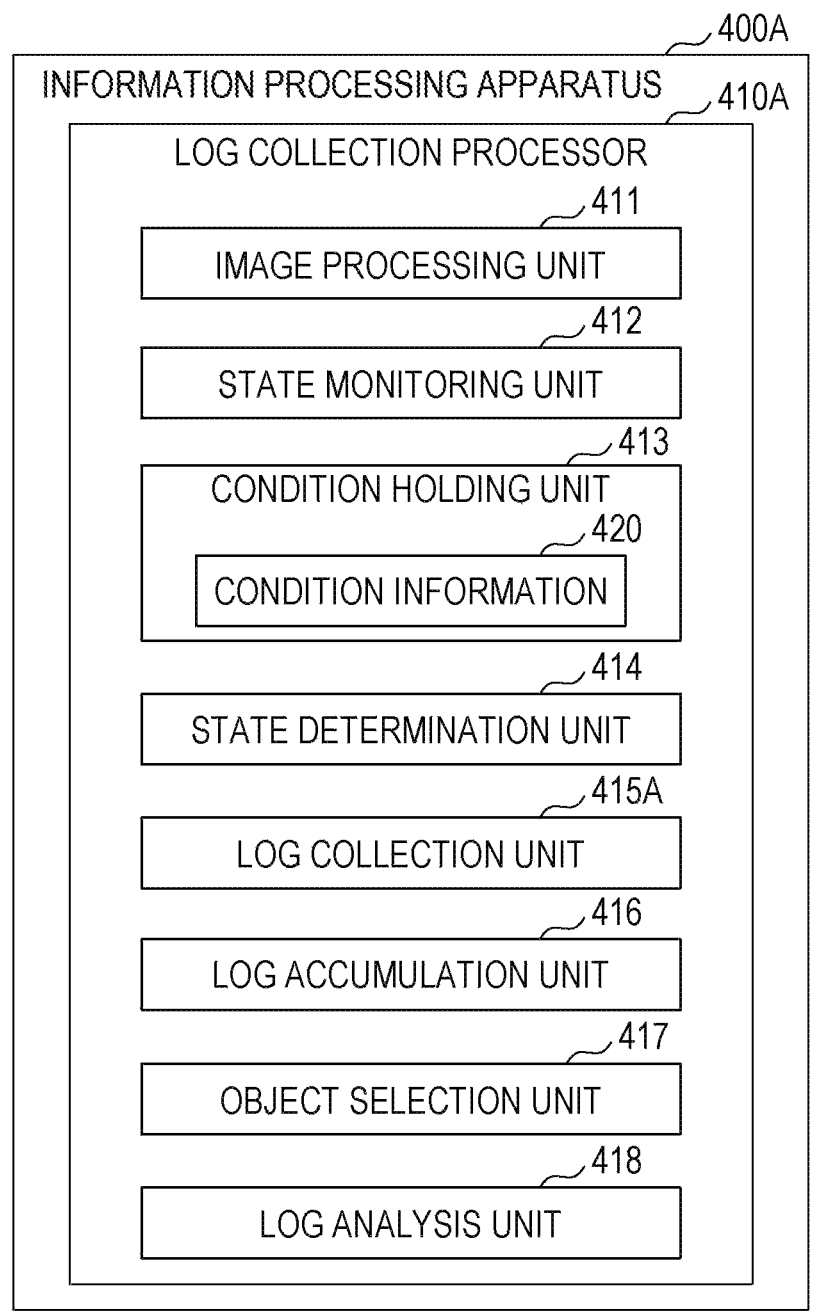
FIG. 9 is a diagram illustrating functions of an information processing apparatus according to a second embodiment.

Next, with reference to FIG. 9, description is given of functions of an information processing apparatus 400A according to the present embodiment. FIG. 9 is a diagram illustrating functions of the information processing apparatus 400A according to the second embodiment.

The information processing apparatus 400A according to the present embodiment includes a log collection processor 410A. The log collection processor 410A according to the present embodiment includes the image processing unit 411, the state monitoring unit 412, the condition holding unit 413, the state determination unit 414, a log collection unit 415A, the log accumulation unit 416, an object selection unit 417, and a log analysis unit 418.

When an object is selected by the object selection unit 417, the log collection unit 415A associates collected log information with an object. In other words, the log collection unit 415A includes information identifying the selected object in the log information. The information identifying the object is, for example, a name of the object or the like, which may uniquely identify the object.

When it is determined by the state determination unit 414 that the state of the user is a high attention state, the object selection unit 417 in the present embodiment selects an object that is the target of attention.

For example, the object selection unit 417 may select, as the object that is the target of attention, an object within a predetermined range from the position of the user in an eye direction of the user in a virtual space when it is determined that the state of the user is the high attention state. The predetermined range may be preset or calculated from previous log information and the like.

Alternatively, the object selection unit 417 may select an object present in the eye direction of the user, as the object that is the target of attention. In other words, the object selection unit 417 may select an object at which the user is directly looking, from an intersection point (collision point) between the eye direction of the user and the object, as the object that is the target of attention.

For example, the object selection unit 417 in the present embodiment selects the object that is the target of attention, depending on a relationship between the position of the user determined to be in the high attention state and the position of each object disposed in the virtual space. Information indicating the position of each of the objects disposed in the virtual space may be held by the image processing unit 411 and the like.

The log analysis unit 418 in the present embodiment analyzes log information accumulated by the log accumulation unit 416. The log analysis unit 418 may perform analysis, for example, by referring to log information accumulated in a log information database 510 in the log accumulation device 500. The log analysis unit 418 may analyze the log information before the log information is stored in the log information database 510 by the log accumulation unit 416 after collected by the log collection unit 415.

The log analysis unit 418 in the present embodiment may acquire information indicating voice pitch from information indicating a speech waveform, for example. The log analysis unit 418 may also have a speech recognition function to convert speech content of the user, from the information indicating the speech waveform, into text data.

The log analysis unit 418 in the present embodiment may determine the user's impression of the object according to the voice pitch, speech content, viewpoint retention time, viewpoint behavior, and heart rate fluctuations from the log information for each object, and may output the determination result as an evaluation of the object.

For example, as for the voice pitch, speech content, viewpoint retention time, viewpoint behavior, and heart rate fluctuations, the log analysis unit 418 may have conditions set therein for determining whether the user's impression is good or bad.

For example, the log analysis unit 418 may previously hold positive words for the object, such as "nice", "interesting", and "want to see more", and may determine that the user's impression of the object is good when the speech content includes any of such words.

For example, the log analysis unit 418 may hold a threshold for the heart rate fluctuation range and a threshold for the viewpoint retention time, and may determine that the user's impression of the object is bad when the heart rate fluctuation range is not less than the threshold and the viewpoint retention time is less than the threshold.

In the log analysis unit 418 in the present embodiment, the conditions for determining the user's impression of the object may be arbitrarily set by an administrator of the information processing apparatus 400A, or the like.

Figure 10:
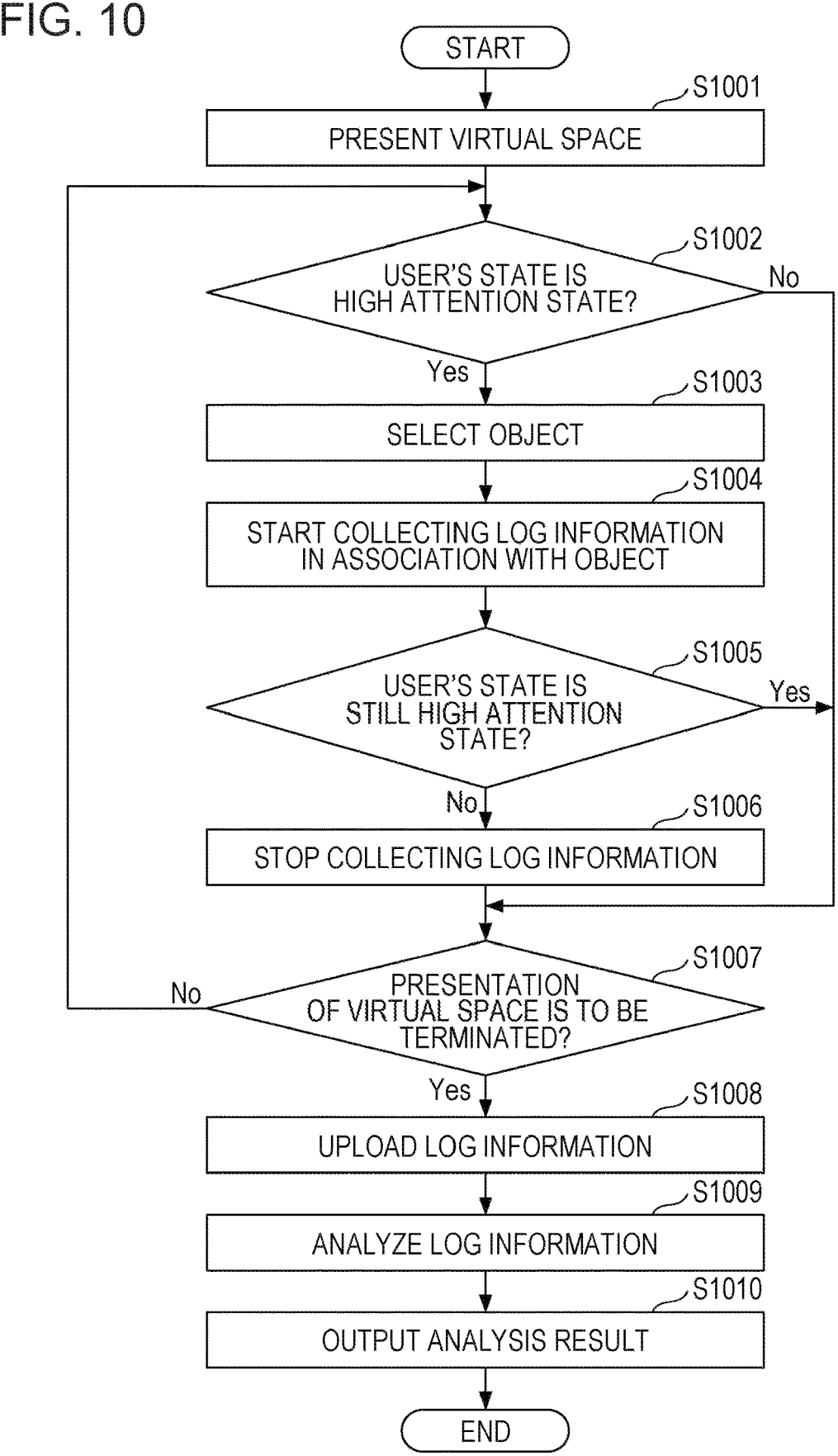
FIG. 10 is a first flowchart illustrating operations of an information processing apparatus according to a second embodiment.

Hereinafter, with reference to FIG. 10, description is given of operations of the information processing apparatus 400A according to the present embodiment. FIG. 10 is a first flowchart illustrating the operations of the information processing apparatus according to the second embodiment.

Upon receipt of an instruction to present a virtual space, the information processing apparatus 400A according to the present embodiment uses the image processing unit 411 to output image data of an image indicating the virtual space to the display device 200, and starts presenting the virtual space to the user wearing the display device 200 (Step S1001).

Then, the information processing apparatus 400A uses the state monitoring unit 412 to monitor monitoring target information outputted from the display device 200 and the sensor group 300, and uses the state determination unit 414 to determine whether or not the monitoring target information satisfies the condition information 420 in the condition holding unit 413 (Step S1002). In other words, the state determination unit 414 determines, based on the monitoring target information, whether or not the state of the user is a high attention state.

When the state of the user is not determined to be the high attention state in Step S1002, that is, when it is determined that the state of the user is not the high attention state, the information processing apparatus 400A advances to Step S1007 to be described later.

When it is determined in Step S1002 that the state of the user is the high attention state, the information processing apparatus 400A uses the object selection unit 417 to select an object that is the target of attention (Step S1003).

Subsequently, the information processing apparatus 400A uses the log collection unit 415A to start collecting log information in association with the selected object (Step S1004), and then advances to Step S1005.

The processing from Step S1005 to Step S1008 in FIG. 10 is similar to the processing from Step S604 to Step S607 in FIG. 6, and thus description thereof is omitted.

After Step S1008, the information processing apparatus 400A uses the log analysis unit 418 to analyze the log information (Step S1009), and outputs the analysis result (Step S1010) before terminating the processing.

Analysis result information indicating the analysis result outputted here may be stored in the log information database 510 in association with the selected object, as in the case of the log information. The analysis result information may be accumulated in the log information database 510 as a part of the log information.

Figure 11:
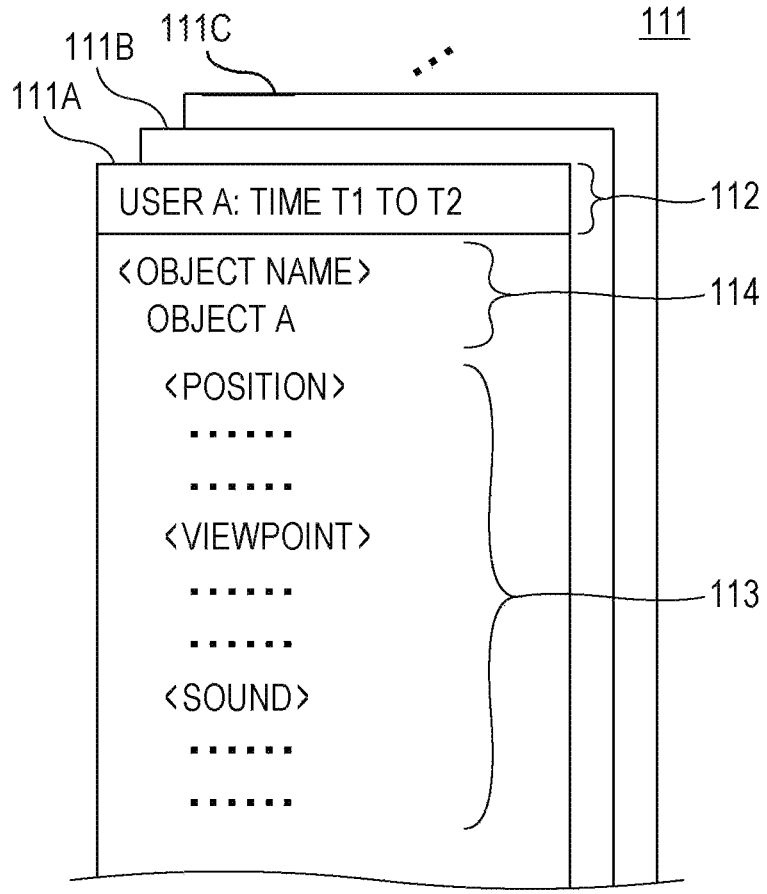
FIG. 11 is a diagram illustrating an example of log information according to a second embodiment.

Hereinafter, with reference to FIG. 11, description is given of log information collected by the log collection unit 415A. FIG. 11 is a diagram illustrating an example of log information according to the second embodiment.

Log information 111 in the present embodiment includes log information 111A acquired in the time period T12, log information 111B acquired in the time period T34, and log information 111C acquired in the time period T56.

The log information 111A includes information 112, information 113, and information 114. The information 112 includes user identification information and the time period during which the log information is collected. The information 113 is information collected by the log collection unit 415A. The information 114 is information identifying the object selected as the target of attention.

In the log information 111A, the object selected as the target of attention is the object A. Therefore, the information 114 has the name "object A".

As in the case of the log information 111A, the log information 111B includes "object B" that is the name of the object selected as the target of attention in the time period T34. Likewise, the log information 111C includes "object C" that is the name of the object selected as the target of attention in the time period T56.

Figure 12:
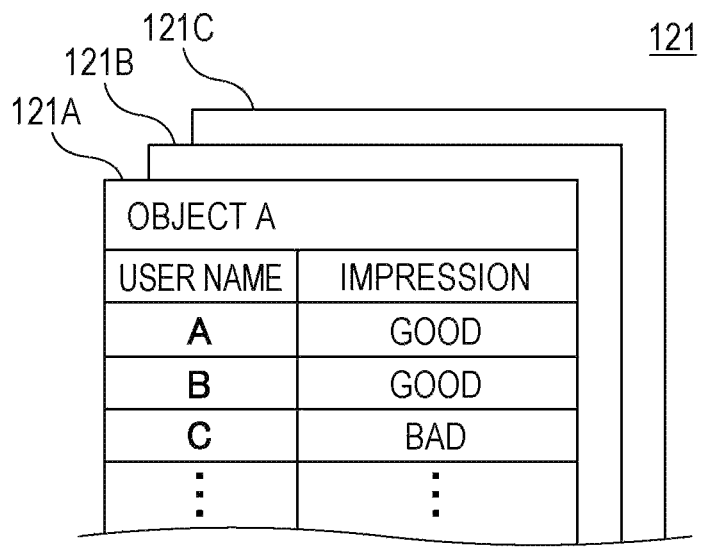
FIG. 12 is a diagram illustrating an example of an analysis result of log information according to a second embodiment.

Next, with reference to FIG. 12, description is given of a log information analysis result obtained by the log analysis unit 418 in the present embodiment. FIG. 12 is a diagram illustrating an example of the log information analysis result according to the second embodiment.

FIG. 12 illustrates an example of the case where favorability for each object is outputted for each user as the result of analysis of log information acquired for each object by the log analysis unit 418. The analysis result obtained by the log analysis unit 418 may be displayed on a display or the like in the information processing apparatus 400A or outputted to an external device from the information processing apparatus 400A, for example.

Analysis result information 121 indicating the analysis results illustrated in FIG. 12 include analysis result information 121A, 121B, and 121C indicating the analysis results for the objects A, B, and C, respectively.

In the analysis result information 121A, information identifying the object A, information identifying the user to whom the virtual space is presented, and information indicating the impression of the object A for each user are associated with each other. In the example of FIG. 12, the information identifying the object A is the name of the object A, and the information identifying the user is a user name.

In the analysis result information 121A, the user having the user name "A" and the user having the user name "B" have a good impression of the object A, while the user having the user name "C" has a bad impression.

As described above, in the present embodiment, when it is determined that the state of the user is the high attention state, the evaluation from the user may be obtained for each object by selecting the object that is the target of attention and by accumulating and analyzing the log information for each selected object.

Although the information associating the impressions given to the respective users for each object is used as the analysis result information in the example of FIG. 12, the information outputted as the analysis result is not limited thereto.

For example, the information processing apparatus 400A may calculate a value indicating favorability for each object, based on the analysis result information 121 illustrated in FIG. 12, and then output the result thereof as the analysis result information.

In the present embodiment, the log analysis unit 418 may output information indicating a particular region to which attention is paid by the user within an object selected by the object selection unit 417, from the trajectory of the user's viewpoint within the selected object, for example, as the analysis result information.

For example, a case is considered where the virtual space indicates a space inside a store having products placed on display and an object corresponding to a certain product is selected as an object drawing attention.

In this case, the selected object is an image indicating a package of the product. Therefore, information indicating a particular region to which attention is paid by the user within the object is information identifying content particularly likely to draw attention in the package. This information is useful, for example, in examining whether or not the user in the virtual space is paying attention to the content intended by the designer of the package, or the like.

Figure 13A:
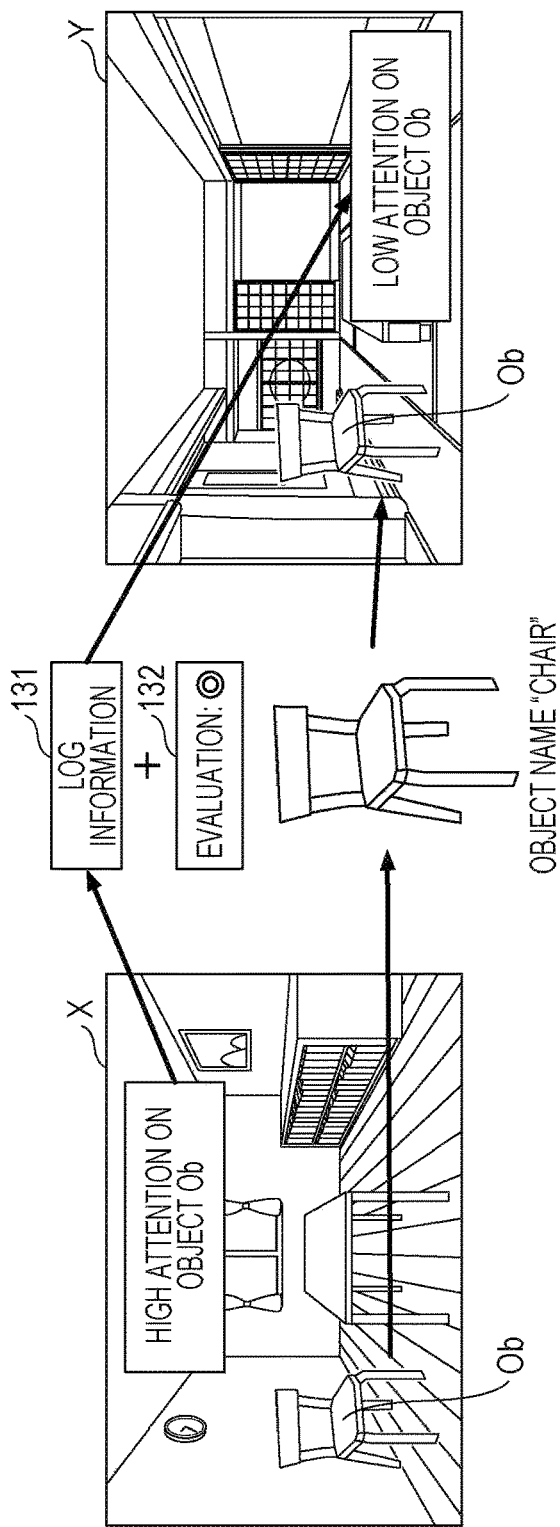
FIGS. 13A and 13B are diagrams illustrating an effect achieved by accumulation of log information according to a second embodiment.
Figure 13B:
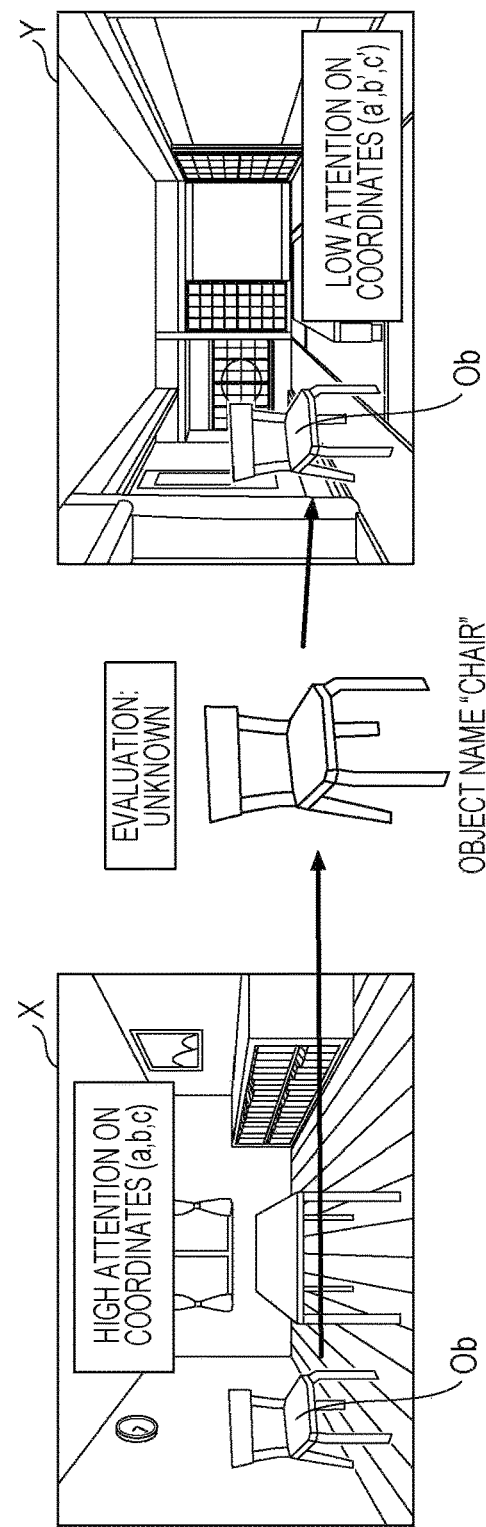

Next, with reference to FIGS. 13A and 13B, description is given of an effect achieved by accumulating the log information for each object.

FIGS. 13A and 13B are diagrams illustrating an effect achieved by accumulating log information according to the second embodiment. FIG. 13A is a diagram illustrating a case where the present embodiment is applied, while FIG. 13B is a diagram illustrating a case where the present embodiment is not applied.

In the present embodiment, FIG. 13A illustrates a case where an object Ob having a name "chair" is disposed in a virtual space X and in a virtual space Y.

In the virtual space X, log information 131 associated with the object Ob and information 132 indicating evaluation of the log information 131, as analysis result information for the log information 131, are acquired. The double circle in the information 132 indicates a good impression.

As may be seen from such information, the object Ob is selected as the object drawing attention in the virtual space X. As may be seen from the information 132 indicating the evaluation result, the object Ob in the virtual space X gives the user a good impression.

That is, it may be seen that, in the virtual space X, the object Ob is the object drawing a lot of attention from the user and giving the user a good impression.

On the other hand, no log information associated with the object Ob is acquired in the virtual space Y. Therefore, it may be seen that, in the virtual space Y, the object Ob is not selected as the object drawing attention and does not draw much attention from the user.

In this event, it is clear that the object Ob draws a lot of attention and gives a good impression in the virtual space X. Therefore, it may be seen that the reason why the object Ob does not draw much attention in the virtual space Y is because of the compatibility between the object Ob and the virtual space Y.

Meanwhile, in the example of FIG. 13B where the present embodiment is not applied, the object Ob is managed as coordinate information in each of the virtual spaces X and Y.

Therefore, when log information is acquired in the virtual space X, for example, it may be seen from the log information that the object Ob disposed at coordinates (a, b, c) in the virtual space X draws a lot of attention. When log information is acquired in the virtual space Y, it may be seen from the log information that the object Ob at coordinates (a', b', c') in the virtual space Y does not draw much attention.

However, in FIG. 13B, the object Ob is recognized as the object disposed at the coordinates (a, b, c) in the virtual space X, and is recognized as the object disposed at the coordinates (a', b', c') in the virtual space Y. Therefore, in FIG. 13B, it is not possible to determine whether or not the same object is disposed in the virtual spaces X and Y. Therefore, it may only be seen from FIG. 13B that the object at the coordinates (a', b', c') in the virtual space Y does not draw much attention, making it difficult to estimate the cause of low attention.

As described above, in the present embodiment, log information and analysis result information for the log information are accumulated in association with each other for each object. Therefore, the object may be set in a plurality of different virtual spaces to perform examination of a relationship between the virtual spaces and attention drawn to the object, and the like.

According to the present embodiment, even when the object is a mobile body such as a vehicle and may not be associated with coordinates, for example, log information and analysis result information for the log information are accumulated in association with each other for each object.

Although the log collection processor 410A analyzes log information after collecting the log information and then stores the log information and the analysis result information in the log information database 510 in the example of FIG. 10, the embodiments are not limited thereto.

In the present embodiment, only the analysis result information for the log information may be stored in the log information database 510.

Figure 14:
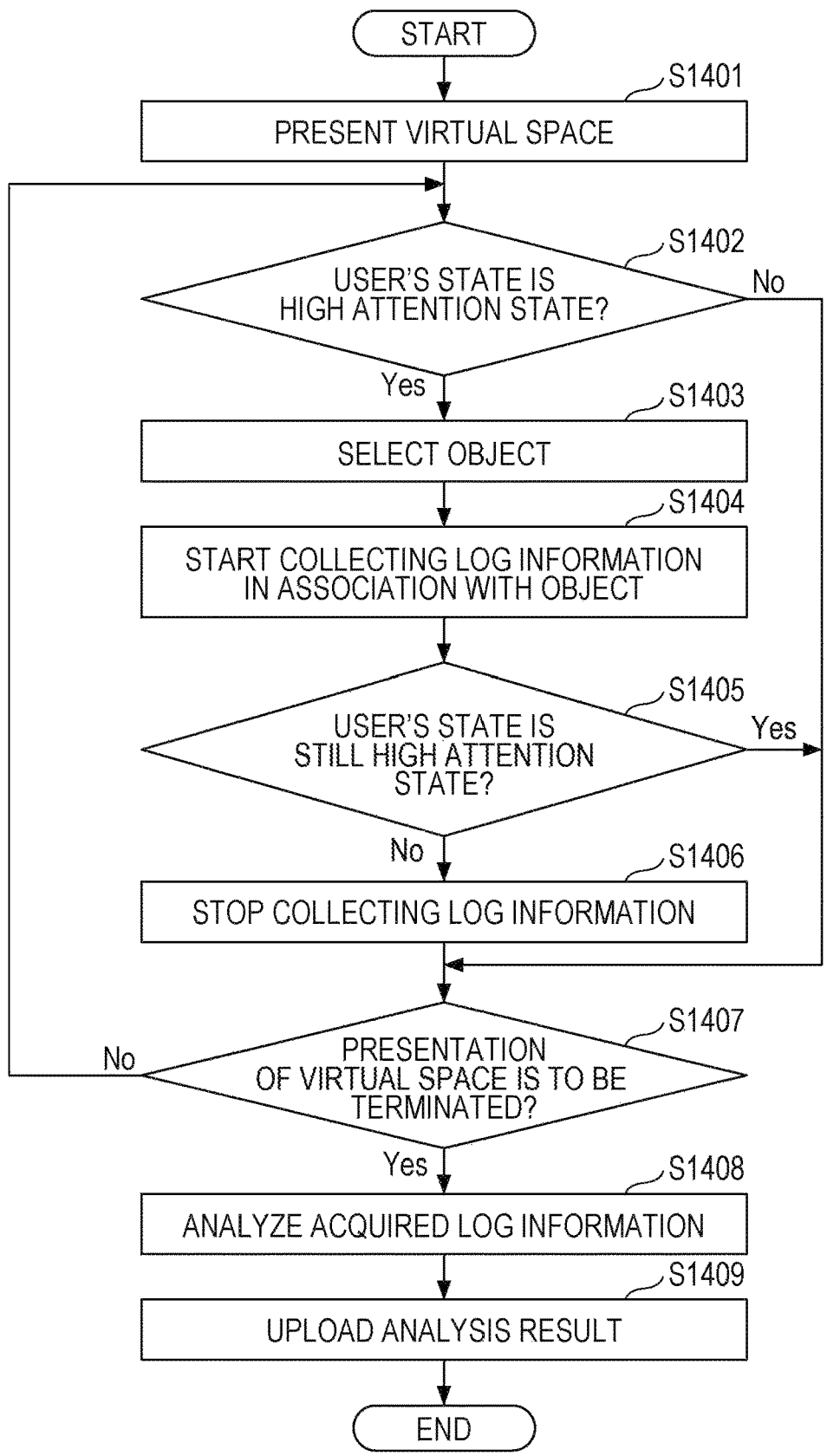
FIG. 14 is a second flowchart illustrating operations of an information processing apparatus according to a second embodiment.

FIG. 14 is a second flowchart illustrating operations of the information processing apparatus according to the second embodiment.

The processing from Steps S1401 to S1407 in FIG. 14 is the same as the processing from Steps S1001 to S1007 in FIG. 10, and thus description thereof is omitted.

When the presentation of the virtual space is to be terminated in Step S1407, the information processing apparatus 400A uses the log analysis unit 418 to analyze the log information collected by the log collection unit 415 (Step S1408).

Subsequently, the information processing apparatus 400A uses the log accumulation unit 416 to upload and accumulate the analysis result information indicating the analysis result obtained by the log analysis unit 418 to the log accumulation device 500 (Step S1409) and then terminates the processing.

Accordingly, by accumulating only the analysis result information for the log information in the log accumulation device 500, memory capacity desired for the log accumulation device 500 may be reduced compared with the case where the log information is accumulated.

Third Embodiment

Hereinafter, a third embodiment is described with reference to the drawings. The third embodiment is different from the second embodiment in that conditions for determining whether or not the state of the user is a high attention state are set for each object. Therefore, in the following description of the third embodiment, similar functional configurations to those in the second embodiment are denoted by the same reference numerals used in the description of the second embodiment, and description thereof is omitted.

Figure 15:
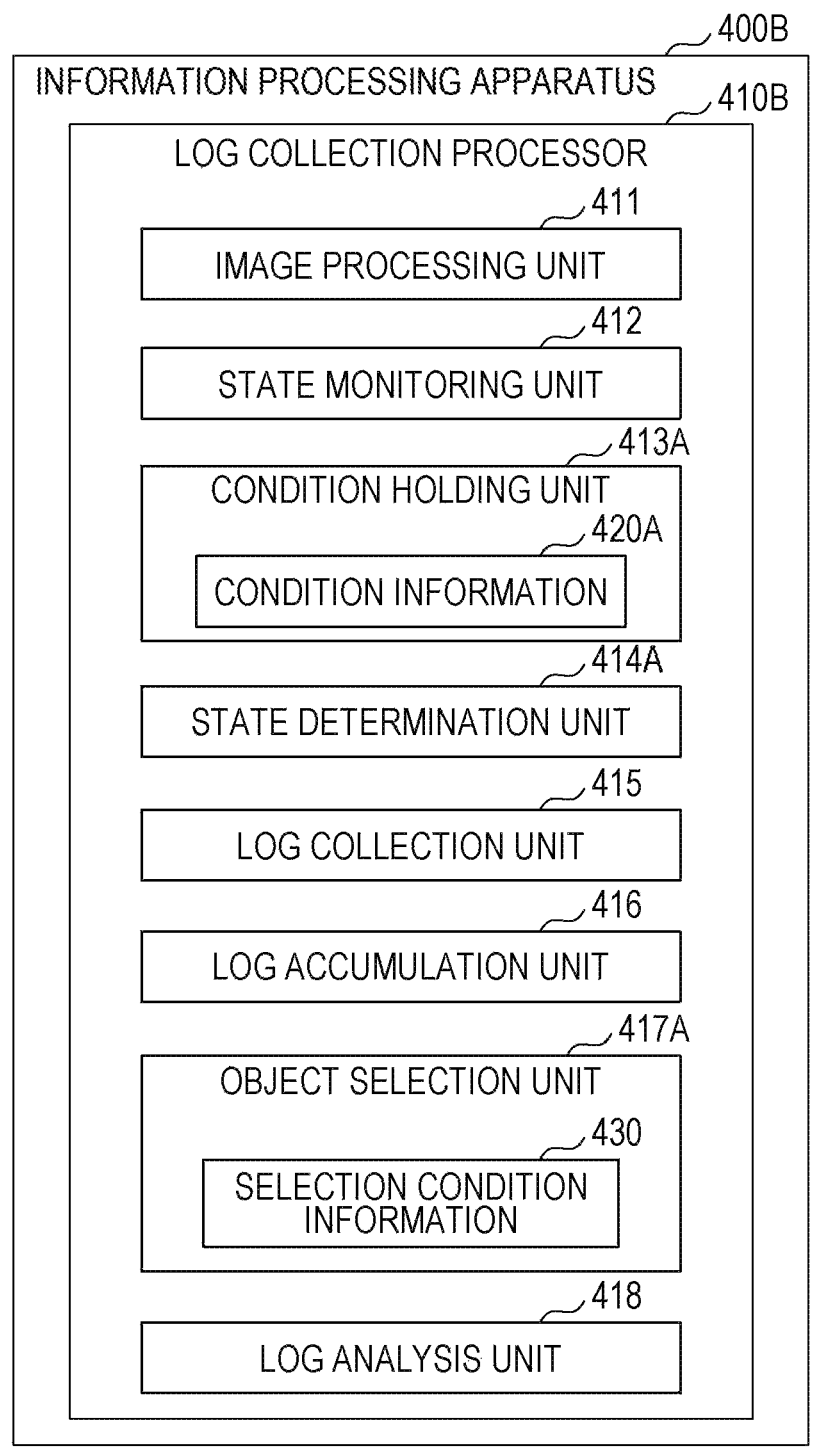
FIG. 15 is a diagram illustrating functions of an information processing apparatus according to a third embodiment.

FIG. 15 is a diagram illustrating functions of an information processing apparatus 400B according to the third embodiment. The information processing apparatus 400B according to the present embodiment includes a log collection processor 410B.

The log collection processor 410B includes the image processing unit 411, the state monitoring unit 412, a condition holding unit 413A, a state determination unit 414A, the log collection unit 415, the log accumulation unit 416, an object selection unit 417A, and the log analysis unit 418.

The condition holding unit 413A in the present embodiment holds condition information 420A. In the condition information 420A, conditions for determining whether or not the state of the user is a state where the user is paying attention to a specific object are set for each object. The condition information 420A is described in detail later.

The object selection unit 417A in the present embodiment holds selection condition information 430. In the selection condition information 430, an object selection method is set for each object. The selection condition information 430 is described in detail later.

The state determination unit 414A in the present embodiment determines whether or not monitoring target information monitored by the state monitoring unit 412 satisfies any of the condition information 420A.

The object selection unit 417A uses the state determination unit 414A to select an object drawing attention by using a selection method corresponding to the object corresponding to the condition satisfied by the monitoring target information.

Hereinafter, with reference to FIGS. 16A and 16B, description is given of the condition information 420A and the selection condition information 430 in the present embodiment. FIGS. 16A and 16B are diagrams respectively illustrating examples of the condition information and the selection condition information according to the third embodiment. FIG. 16A illustrates an example of the condition information 420A, while FIG. 16B illustrates an example of the selection condition information 430.

In the condition information 420A according to the present embodiment, an object type, an item, and a condition are associated with each other.

The object type is the type of an object disposed in a virtual space. In the example of FIGS. 16A and 16B, the object type includes, for example, a sound source emitting a sound, a building and space, an object, and a source generating a smell.

The item is an item of information included in the monitoring target information. The condition is set for each object type.

In FIG. 16A, when the object type is "sound source", for example, a user is determined to be in a state of paying attention to the object "sound source" when the position of the user included in the monitoring target information is within a predetermined range from the position of the sound source and does not satisfy conditions corresponding to other object types.

In FIG. 16A, when the object type is "building, space", for example, a user is determined to be in a state of paying attention to the object "building, space" when the position of the user's viewpoint stays or moves within the object for a certain period of time or more and the position of the user is within a predetermined range from the object.

For example, when the viewpoint of the user moves on a certain building object and the position of the user falls within a predetermined range from the object after the user approaches the object, the user is determined to be in a state of paying attention to the building object.

As described above, in the present embodiment, the conditions for determining whether or not the state of the user is the high attention state are set for each object.

In the selection condition information 430 according to the present embodiment, the object type, the item, and a selection method are associated with each other.

In FIG. 16B, when the object type is "sound source", for example, an object within a predetermined range, within which a sound may be heard, from the position of the user included in the monitoring target information is selected. In this case, again, the predetermined range may be set according to the volume of the sound emitted from the sound source.

In FIG. 16B, when the object type is "building, space", for example, an object at a position within a predetermined range from the position of the user is selected.

Therefore, in the present embodiment, for example, it is assumed that the state determination unit 414A determines that the user is in a state of paying attention to the object "sound source" by referring to the condition information 420A. In this case, the object selection unit 417 selects the sound source within a predetermined range from the position of the user, as the object drawing attention, by referring to the selection condition information 430.

The condition information 420A and the selection condition information 430 may be previously set for each virtual space. The selection condition information 430 may be inputted to the information processing apparatus 400B at the same time as when the image data of the image indicating the virtual space is inputted to the information processing apparatus 400B.

Although the item of the monitoring target information and the condition are associated with the object type in the example of FIGS. 16A and 16B, the embodiments are not limited thereto. In the selection condition information 430, for example, the item of the monitoring target information and the condition may be associated with individual objects.

Figure 17:
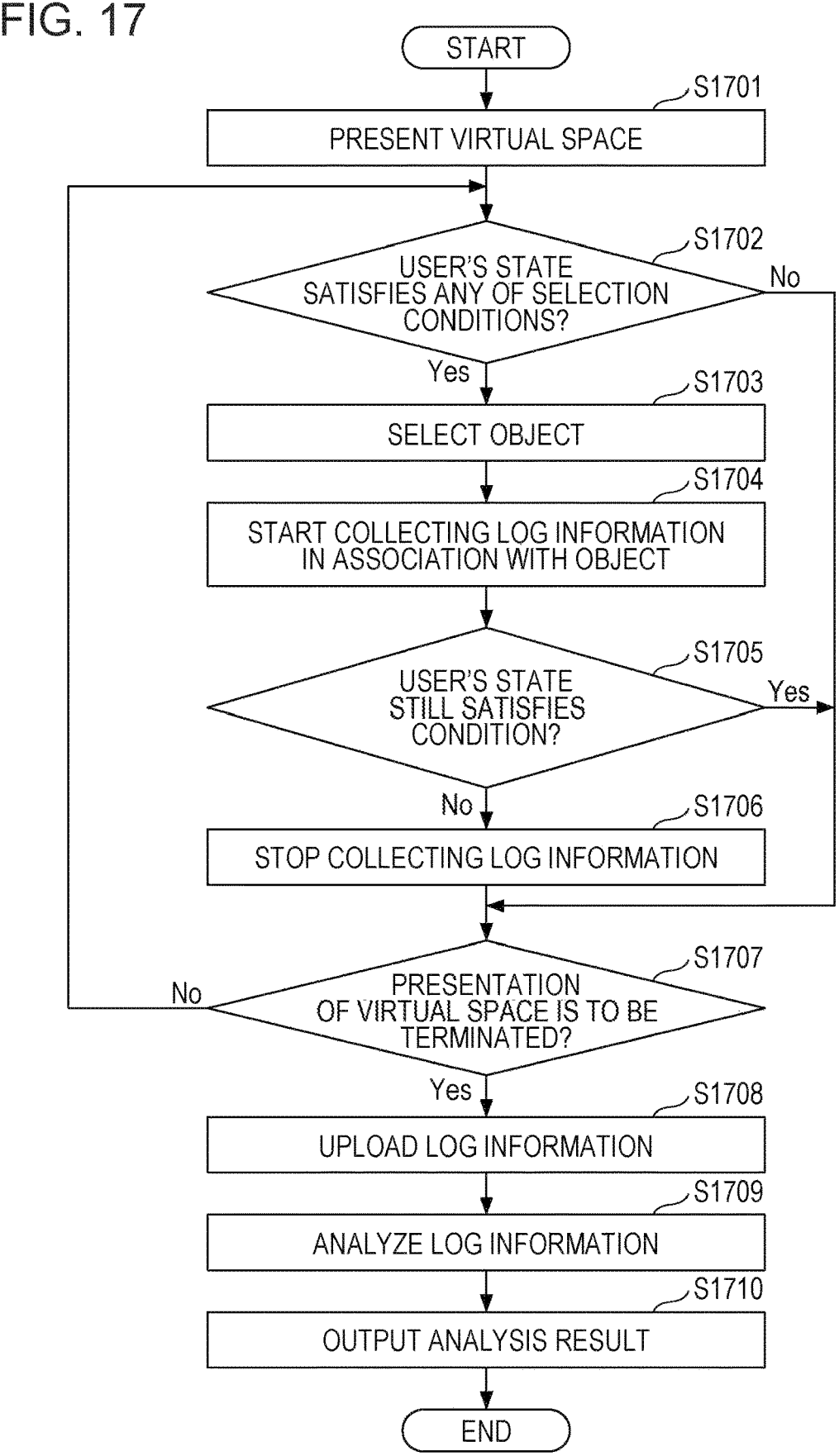
FIG. 17 is a flowchart illustrating operations of an information processing apparatus according to a third embodiment.

Hereinafter, with reference to FIG. 17, description is given of operations of the information processing apparatus 400B according to the third embodiment. FIG. 17 is a flowchart illustrating the operations of the information processing apparatus 400B according to the third embodiment.

Upon receipt of an instruction to present a virtual space, the information processing apparatus 400B according to the present embodiment uses the image processing unit 411 to output image data of an image indicating the virtual space to the display device 200, and starts presenting the virtual space to the user wearing the display device 200 (Step S1701).

Then, the information processing apparatus 400B uses the state determination unit 414A to determine, based on the monitoring target information, whether or not the state of the user satisfies any of the conditions included in the condition information 420A in the condition holding unit 413A (Step S1702).

When the state of the user indicated by the monitoring target information satisfy none of the conditions included in the condition information 420A in Step S1702, the information processing apparatus 400B advances to Step S1707 to be described later.

When the state of the user indicated by the monitoring target information satisfies any of the conditions included in the condition information 420A in Step S1702, the information processing apparatus 400B uses the object selection unit 417A to select an object drawing attention, based on an object selection method corresponding to the condition satisfied by the monitoring target information (Step S1703).

Thereafter, the information processing apparatus 400B uses the log collection unit 415 to start collecting log information associated with the selected object (Step S1704).

Subsequently, the information processing apparatus 400B determines whether or not the state of the user still satisfies the condition once satisfied, based on the monitoring target information (Step S1705). In other words, the information processing apparatus 400B determines whether or not the state of the user is a state where the attention to the selected object is lowered.

When the state of the user still satisfies the condition in Step S1705, the information processing apparatus 400B advances to Step S1707 to be described later.

When the state of the user no longer satisfies the condition once satisfied in Step S1705, the information processing apparatus 400B stops the log information collection by the log collection unit 415 (Step S1706) and then advances to Step S1707 to be described later.

The processing from Steps S1707 to S1710 is similar to the processing from Steps S1007 to S1010 in FIG. 10, and thus description thereof is omitted.

As described above, in the present embodiment, the conditions for determining the user's attention to the object are set for each object type. Therefore, according to the present embodiment, log information concerning the object to which the user pays attention may be acquired and accumulated.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium having stored therein a program that causes a computer to execute a process, the process comprising:
   determining when attention of a user that views a virtual space in a virtual reality environment to an object of a plurality of objects disposed in the virtual space is increased, based on a viewpoint of the user being retained for at least a predetermined amount of time, and at least one of heart rate of the user being at least a predetermined rate and sound volume of a voice of the user being at least a predetermined level; and
   when the attention of the user is determined to be increased, selecting an object of the plurality of objects disposed in the virtual space based on at least one of an eye direction of the user and a position of the user in the virtual space,
   wherein different values of the predetermined amount of time, different values of the predetermined rate and different values of the predetermined level are settable for each object of the plurality of objects disposed in the virtual space.

2. The non-transitory computer-readable recording medium according to claim 1, wherein
   the selected object is disposed, in the eye direction of the user in the virtual space, within a predetermined range from the position of the user.

3. The non-transitory computer-readable recording medium according to claim 1, wherein
   the selected object is disposed along the eye direction of the user in the virtual space.

4. The non-transitory computer-readable recording medium according to claim 1, wherein
   a selection method for selecting an object is set for each object of the plurality of objects, and
   the selecting selects an object of the plurality of objects for which the attention of the user is determined to be increased and that satisfies a condition of the selection method for the object.

5. The non-transitory computer-readable recording medium according to claim 1, wherein
   the viewpoint of the user is acquired using a camera provided in a display device that displays the virtual space, the sound volume of the voice of the user is acquired using a microphone provided in the display device, and the heart rate of the user is acquired using a heart rate sensor.

6. The non-transitory computer-readable recording medium according to claim 1, the process further comprising:
   when the attention of the user is determined to be increased, starting collection of log information in association with the selected object, and
   stopping the collection of the log information when the attention of the user is no longer increased,
   wherein the collected log information includes the viewpoint, the at least one of heart rate and sound volume, and an indication of a time during which the attention of the user was increased, in association with the selected object.

7. The non-transitory computer-readable recording medium according to claim 6, the process further comprising:
   analyzing the collected log information; and
   outputting result information indicating a result of the analysis.

8. The non-transitory computer-readable recording medium according to claim 7, the process further comprising:
   accumulating, in association with the selected object, the result information.

9. A method, comprising:
   determining, by a computer, when attention of a user that views a virtual space in a virtual reality environment to an object of a plurality of objects disposed in the virtual space is increased, based on a viewpoint of the user being retained for at least a predetermined amount of time, and at least one of heart rate of the user being at least a predetermined rate and sound volume of a voice of the user being at least a predetermined level; and
   when the attention of the user is determined to be increased, selecting an object of the plurality of objects disposed in the virtual space based on at least one of an eye direction of the user and a position of the user in the virtual space,
   wherein different values of the predetermined amount of time, different values of the predetermined rate and different values of the predetermined level are settable for each object of the plurality of objects disposed in the virtual space.

10. The method according to claim 9, further comprising:
    when the attention of the user is determined to be increased, starting collection of log information in association with the selected object, and
    stopping the collection of the log information when the attention of the user is no longer increased,
    wherein the collected log information includes the viewpoint, the at least one of heart rate and sound volume, and an indication of a time during which the attention of the user was increased, in association with the selected object.

11. An information processing apparatus, comprising:
    a memory; and
    a processor coupled to the memory, and the processor is configured to:
      determine when attention of a user that views a virtual space in a virtual reality environment to an object of a plurality of objects disposed in the virtual space is increased, based on a viewpoint of the user being retained for at least a predetermined amount of time, and at least one of heart rate of the user being at least a predetermined rate and sound volume of a voice of the user being at least a predetermined level, and
      when the attention of the user is determined to be increased, select an object of the plurality of objects disposed in the virtual space based on at least one of an eye direction of the user and a position of the user in the virtual space, wherein different values of the predetermined amount of time, different values of the predetermined rate and different values of the predetermined level are settable for each object of the plurality of objects disposed in the virtual space.

12. The information processing apparatus according to claim 11, wherein the processor is figured to:

when the attention of the user is determined to be increased, start collection of log information in association with the selected object, and stop the collection of the log information when the attention of the user is no longer increased, and the collected log information includes the viewpoint, the at least one of heart rate and sound volume, and an indication of a time during which the attention of the user was increased, in association with the selected object.

* * * * *